United States Patent [19]
Mohan et al.

[11] Patent Number: 6,123,080
[45] Date of Patent: Sep. 26, 2000

[54] DRAPE

[75] Inventors: Narendra Mohan; Alan Waters, both of Bristol, United Kingdom

[73] Assignee: AMBA Medical Limited, Bristol, United Kingdom

[21] Appl. No.: 09/217,481

[22] Filed: Dec. 21, 1998

[30] Foreign Application Priority Data

Oct. 27, 1998 [GB] United Kingdom .................. 9823492

[51] Int. Cl.⁷ .................................................. A61B 19/00
[52] U.S. Cl. ........................................... 128/849; 128/856
[58] Field of Search .................................... 128/849–856; 600/121, 124; 359/510, 511

[56] References Cited

U.S. PATENT DOCUMENTS

| 4,069,913 | 1/1978 | Harrigan | 128/856 |
| 5,433,221 | 7/1995 | Adair | 128/856 |
| 5,496,259 | 3/1996 | Perkins | 600/124 |
| 5,765,565 | 6/1998 | Adair | 128/856 |

OTHER PUBLICATIONS

Amba Medical Limited Product Catalogue.

*Primary Examiner*—Michael A. Brown
*Attorney, Agent, or Firm*—Townsend and Townsend and Crew

[57] ABSTRACT

There is provided a novel drape for covering surgical equipment, particularly but not exclusively for covering elongate surgical equipment which flexes during use, such as an endoscopic camera cable. The drape comprises a sleeve and a ring-shaped former. The ring-shaped former is arranged coaxially inside the sleeve, the majority of the latter being multiply folded over and carried on the ring-shaped former. The proximal region of the sleeve contacts the radially outer periphery of the ring-shaped former and it is overlaid with successive sleeve layers arising from repeated 180° folds in the sleeve. Pulling the distal region of the sleeve away from the former causes orderly unfolding of the sleeve by relative sliding of the outermost layer over the adjacent layer.

13 Claims, 2 Drawing Sheets

DRAPE

FIELD OF THE INVENTION

The present invention relates to a drape for covering surgical equipment, particularly but not exclusively for covering elongate surgical equipment which flexes during use, such as an endoscopic camera cable.

BACKGROUND ART

In a surgical environment, it is well known that surgical equipment could be the source of life threatening infections unless thoroughly sanitised. In the case of minimally invasive (key-hole) surgical procedures, the need for sterile conditions is still paramount in spite of the fact that the size of incisions and internal exposure of the patient to equipment are significantly reduced. Thus, a reusable probe introduced into a patient during key-hole surgery must be sterilised before re-use on another patient. However, the sterilisation of certain ancillary equipment, such as cabling which is merely used in conjunction with the probe and not introduced into the patient, would be expensive and time consuming if performed after each operation. Instead, a practice has developed of covering the ancillary equipment with a sterile drape which may be disposed of and replaced after each operation.

Surgical drapes are mass produced to suit a range of different applications. For example, the drapes may be employed to cover varying lengths of cable depending on individual circumstance, and thus a potential problem arises during use concerning temporary storage of drape material which is surplus to requirements in each given situation. To this end, telescopic and concertina style drapes have been proposed in attempts to confine excess drape material in an orderly manner, thereby reducing risk of interference with the surgical procedure being undertaken. However, such drapes require materials capable of retaining intricate shapes, not to mention experienced application, without which the integrity of the sterile covering may be impaired.

An object of the present invention is to provide a drape for covering surgical equipment, with the length of the drape available for covering the surgical equipment being readily variable to suit individual circumstances.

DISCLOSURE OF THE INVENTION

According to the present invention, there is provided a drape for covering surgical equipment, comprising a sleeve having a proximal region and a distal region, and a tubular former on which the sleeve is mounted with the tubular former being a snug fit inside the sleeve whilst providing passage therethrough, wherein the sleeve is movable between a first position where the distal region is folded over the proximal region on the tubular former, and the second position where the distal region extends axially beyond the proximal region on the tubular former.

The drape of the present invention enables only the required length of sleeve to be dispensed or unfurled from the tubular former, whilst the excess remains neatly stored on the tubular former out of harm's way. Preferably, there are multiple folds in the sleeve between the proximal and distal regions, providing a series of overlapping or overlying regions therebetween, when the sleeve is in the first position. In this way, the length of sleeve stored on the tubular former may greatly exceed the length of the tubular former, perhaps by one hundred times or more.

The drape may further comprise a housing adapted to fit over one end of the tubular former, leaving an aperture at the other end through which the distal region of the sleeve extends when in the second position. The housing may provide a protective casing helping to prevent rupture of the sleeve when in the first position. The housing may comprise inner and outer walls defining a recess therebetween into which the sleeve and tubular former are received, with the tubular former being a friction fit over the inner wall. The proximal region of the sleeve may at least in part be trapped between the tubular former and the inner wall of the housing to prevent accidental sleeve detachment from the tubular former.

The tubular former may be ring-shaped, with the proximal and distal regions of the sleeve arranged coaxially over the tubular former when in the first position. The inner and outer walls of the housing may be cylindrical, with the recess therebetween having an annular cross-section in one embodiment.

BRIEF DESCRIPTION OF THE DRAWINGS

An embodiment of the invention will now be described, by way of example, with reference to the accompanying figures, in which.

BEST MODE FOR CARRYING OUT THE INVENTION

Figure 1:
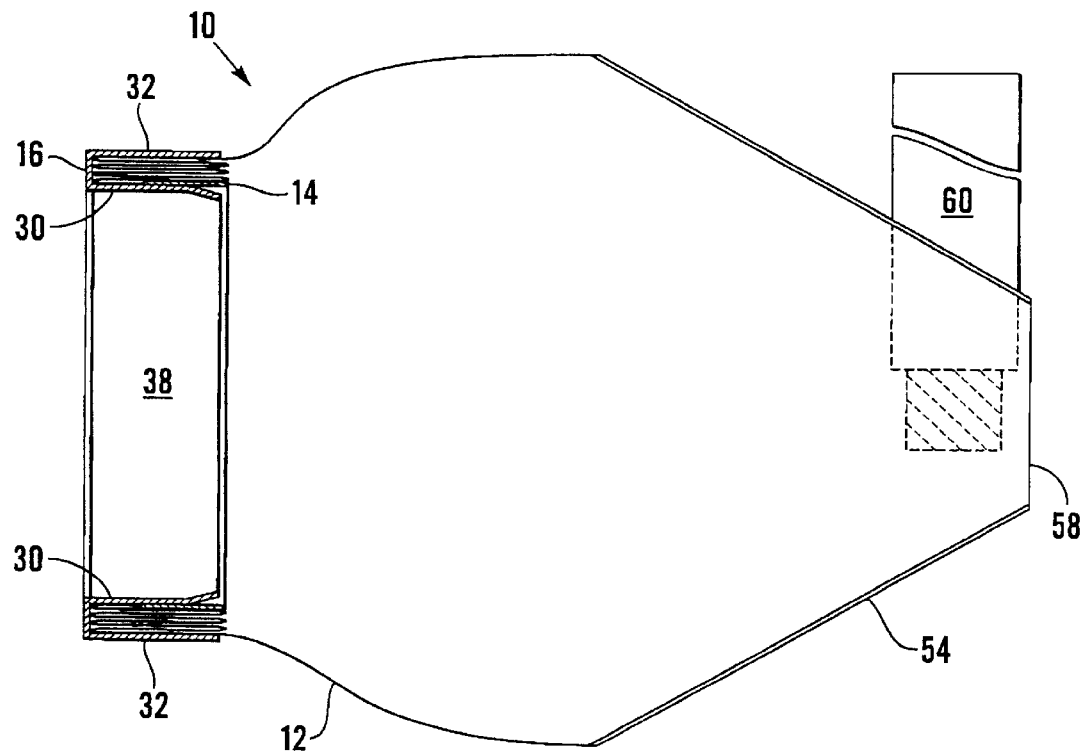
FIG. 1 is a cross-sectional view of a drape embodying the present invention.
Figure 2:
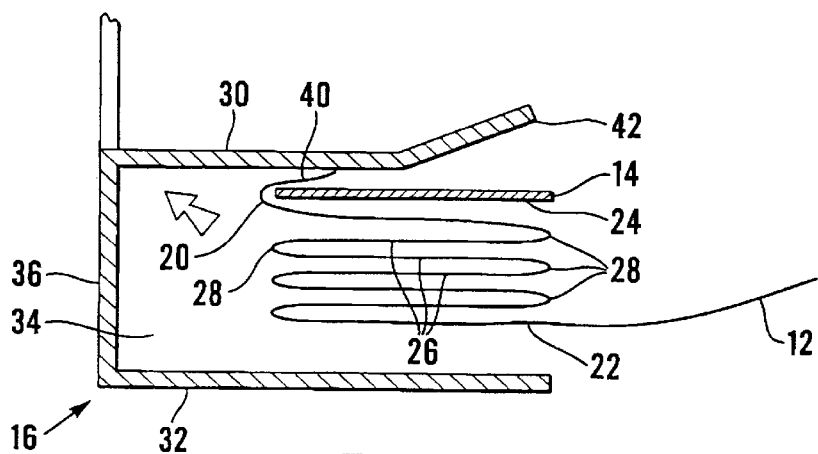
FIG. 2 is a partially exploded schematic showing selected detail of the drape of FIG. 1.

FIGS. 1 and 2 show a drape 10 comprising a sleeve 12, a ring-shaped former 14 and a housing 16. The sleeve 12 has a proximal region 20 and a distal region 22, and consists of LDPE lay flat cubing of length 2.5 metres and sheet thickness $3 \times 10^{-5}$ meters. The ring-shaped former 14 is arranged coaxially inside the sleeve 12, the majority of the latter being multiply folded over and carried on the ring-shaped former 14. The proximal region 20 of the sleeve 12 contacts the radially outer periphery 24 of the ring-shaped former 14 and it is overlaid with successive sleeve layers arising from repeated 180° folds 28 in the sleeve 12. The top or radially outermost layer is part of the distal region 22 of the sleeve 12 and extends axially beyond the ring-shaped former 14. Pulling the distal region 22 away from the former 14 causes orderly unfolding of the sleeve 12 by relative sliding of the outermost layer over the adjacent layer. Each successive sleeve layer 26 which is unfolded from the former adds in turn to the length of the sleeve which is not stored on the ring-shaped former 14.

The housing 16 comprises inner cylindrical wall 30 and outer cylindrical wall 32 which define therebetween a recess 34 of annular cross-section. An end wall 36 extends between the inner and outer cylindrical walls, leaving a bore 38 defined by the inner periphery of the inner cylindrical wall unobstructed to allow for passage of surgical equipment through the housing 16. The recess 34 is adapted to receive the ring-shaped former 14 and any part of the sleeve 12 carried thereon. When housed in the housing, the ring-shaped former 14 is a friction fit over the inner cylindrical wall 30, with friction preventing the former 14 accidentally decoupling from the housing 16. The proximal end 14 of the sleeve 12 is trapped between the former 14 and the inner cylindrical wall 30 to prevent the sleeve from becoming detached from the former 14. The leading edge 42 of the inner cylindrical wall 30 is tapered radially forwards to assist with the positioning of the former 14 and the trapping of the approximal end 40.

Figure 3:
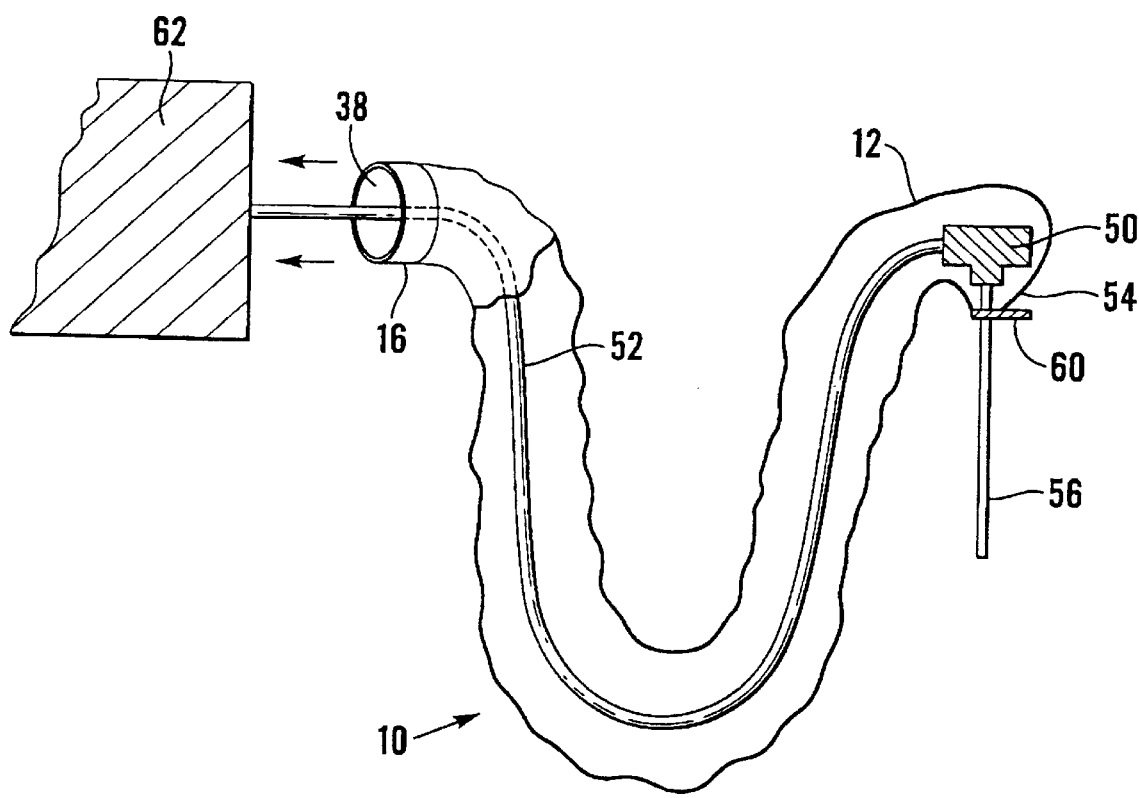
FIG. 3 shows schematically use of the drape of FIG. 1 in covering surgical equipment.

The use of the drape 10 will now be described with reference to FIG. 3. Surgical equipment such as a camera 50 with trailing control cables 52 is introduced through the bore 38 in to the sleeve 12 and positioned in the neck 54 of the distal region 22 of the sleeve 12. A probe 56 for insertion into a patient is attached to the camera through aperture 58 in the sleeve 12, and the latter is thereafter sealed around the probe 56 using surgical tape 60. The sleeve 12 is then unfurled as the housing 16 is moved back along the control cables 52. Once the length of the sleeve extending beyond the ring-shaped former is about the same as the length of the control cables 52, the housing 16 is attached to equipment 62 to complete the enclosure of the cabling and camera. The remaining length of sleeve 12 which is surplus to requirements is retained on ring-shaped former 14.

Once the surgical procedure is completed, the drape 10 is disposed of, and the probe 56 is sterilised. The cabling 52 and camera 50 may be cleaned but thorough sterilisation is unnecessary if they are once again covered by a fresh drape prior to the next surgical procedure on the next patient.

We claim:

1. A drape for covering surgical equipment, comprising a sleeve having a proximal region and a distal region, and a tubular former having a radial outer periphery around which the sleeve is mounted, with the proximal region being a snug fit over the radial outer periphery, wherein the sleeve is moveable between a first position where the distal region is folded over the proximal region on the tubular former, and a second position where the distal region extends axially beyond the proximal region on the tubular former by sliding the distal region over the proximal region, whereby surgical equipment passed into the sleeve through the tubular former is covered by the distal region when the sleeve is in the second position.

2. A drape according to claim 1, in which there are multiple folds in the sleeve between the proximal and distal regions, providing a series of overlapping regions therebetween on the tubular former when the sleeve is in the first position.

3. A drape according to claim 2, in which there are at least 20 overlapping regions between the proximal and distal regions when the sleeve is in the first position.

4. A drape according to claim 3, in which there are at least 50 overlapping regions between the proximal and distal regions when the sleeve is in the first position.

5. A drape according to claim 1, further comprising a housing having a recess adapted to accommodate the tubular former and the sleeve when in the first position.

6. A drape according to claim 5, in which the housing has a bore therethrough which communicates with the inner periphery of the sleeve when the tubular former is received in the recess.

7. A drape according to claim 5, in which the tubular former is a friction fit in the recess in the housing.

8. A drape according to claim 7, in which at least part of the proximal region of the sleeve is trapped between matting surfaces when the tubular former is frictionally held in the recess.

9. A drape according to claim 1, in which the tubular former is ring-shaped, with the proximal and distal regions of the sleeve arranged coaxially over the tubular former when the sleeve is in the first position.

10. A drape for covering surgical equipment, comprising:

a sleeve having a proximal end and a distal end; and a tubular former having an outer periphery and a inner periphery;

wherein the proximal end of the sleeve is coupled to the tubular former, wherein the sleeve is disposed about the outer periphery of the tubular former in a folded arrangement when in a first position, and wherein the distal end of the sleeve may be pulled to a second position where at least a portion of the sleeve is moved off of the tubular former.

11. A drape according to claim 10, further comprising a housing having a recess adapted to accommodate the tubular former and the sleeve when in the first position.

12. A drape according to claim 11, in which the housing has a bore therethrough which communicates with an inner periphery of the sleeve when the tubular former is received in the recess.

13. A drape according to claim 11, in which the tubular former is a friction fit in the recess in the housing.

\* \* \* \* \*